US00PP22681P2

(12) United States Plant Patent
Oudshoorn

(10) Patent No.: US PP22,681 P2
(45) Date of Patent: Apr. 24, 2012

(54) ***MALVA* PLANT NAMED 'POETRY'**

(50) Latin Name: *Malva sylvestris*
Varietal Denomination: Poetry

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/931,680

(22) Filed: Feb. 7, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell

(74) *Attorney, Agent, or Firm* — C. A. Whealy

(57) ABSTRACT

A new and distinct cultivar of *Malva* plant named 'Poetry', characterized by its upright and relatively compact plant habit; moderately vigorous growth habit; bright red purple-colored flowers; and good garden performance.

2 Drawing Sheets

Botanical designation: *Malva sylvestris*.
Cultivar denomination: 'POETRY'.

BACKGROUND OF THE INVENTION

The present invention relates to a new and distinct cultivar of *Malva* plant, botanically known as *Malva sylvestris* and hereinafter referred to by the name 'Poetry'.

The new *Malva* plant is a naturally-occurring branch plant mutation of *Malva sylvestris* 'Park Rondell', not patented. The new *Malva* plant was discovered and selected by the Inventor on a single plant of 'Park Rondell' from within a population of plants of 'Park Rondell' in a controlled environment in Hummelo, The Netherlands.

Asexual reproduction of the new *Malva* plant by softwood cuttings in a controlled environment in Hummelo, The Netherlands since the summer of 2006 has shown that the unique features of this new *Malva* plant are stable and reproduced true to type in successive generations.

SUMMARY OF THE INVENTION

Plants of the new *Malva* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Poetry'. These characteristics in combination distinguish 'Poetry' as a new and distinct *Malva* plant:

1. Upright and relatively compact plant habit.
2. Moderately vigorous growth habit.
3. Bright red purple-colored flowers.
4. Good garden performance.

Plants of the new *Malva* differ primarily from plants of the parent, 'Park Rondell' in flower color as plants of 'Park Rondell' have dark pinkish red-colored flowers.

Plants of the new *Malva* can be compared to plants of *Malva sylvestris* 'Freedom', not patented. In side-by-side comparisons, plants of the new *Malva* differ primarily from plants of 'Freedom' in the following characteristics:

1. Plants of the new *Malva* are more compact than plants of 'Freedom'.
2. Plants of the new *Malva* and 'Freedom' differ in flower color as plants of 'Freedom' have light salmon-colored flowers.

BRIEF DESCRIPTION OF THE PHOTOGRAPHS

The accompanying colored photographs illustrate the overall appearance of the new *Malva* plant showing the colors as true as it is reasonably possible to obtain in colored reproductions of this type. Colors in the photographs may differ slightly from the color values cited in the detailed botanical description which accurately describe the colors of the new *Malva* plant.

The photograph on the first sheet comprises a side perspective view of a typical flowering plant of 'Poetry' grown in an outdoor nursery.

The photograph at the top of the second sheet is a close-up view of a typical flower of 'Poetry'.

The photograph at the bottom of the second sheet is a close-up view of the upper surface of a typical leaf of 'Poetry'.

DETAILED BOTANICAL DESCRIPTION

The aforementioned photographs and following observations, measurements and values describe plants grown during the autumn in an outdoor nursery in Hillegom, The Netherlands and under typical production conditions. During the production of the plants, day temperatures ranged from 12° C. to 26° C. and night temperatures ranged from 4° C. to 18° C. Plants were one year old when the photographs and the description were taken. In the detailed description, color references are made to The Royal Horticultural Society Colour Chart, 2007 Edition, except where general terms of ordinary dictionary significance are used.

Botanical classification: *Malva sylvestris* 'Poetry'.

Parentage: Naturally-occurring branch mutation of *Malva sylvestris* 'Park Rondell', not patented.

Propagation:

*Type.*—By softwood cuttings.

*Time to initiate roots, summer.*—About 20 days at temperatures of 18° C.

*Time to produce a rooted young plant, summer.*—About three months at temperatures of 18° C.

*Root description.*—Thick, fleshy; gray white in color.

*Rooting habit.*—Sparse; density, low.

Plant description:

*Plant and growth habit.*—Upright and relatively compact plant habit; inverted triangle; moderately vigorous growth habit; basal branching habit with about five branches per plant; pinching enhances branching potential.

*Plant height.*—About 117.5 cm.

*Plant width.*—About 59.7 cm.

*Lateral branches.*—Length: About 39.8 cm. Diameter: About 6 mm. Internode length: About 8.4 cm. Texture: Densely pubescent. Strength: Strong. Color: Close to 144A to 144B.

Foliage description:

*Arrangement.*—Alternate; simple.

*Length.*—About 10.8 cm.

*Width.*—About 9.8 cm.

*Shape.*—Cordate; palmately lobed.

*Apex.*—Broadly acute to obtuse.

*Base.*—Cordate.

*Margin.*—Palmately lobed; coarsely crenate.

*Venation pattern.*—Palmate.

*Texture, upper and lower surfaces.*—Rugose; moderately pubescent.

*Color.*—Developing leaves, upper surface: Close to 137B. Developing leaves, lower surface: Close to 147B. Fully developed leaves, upper surface: Close to N137A and 147A; venation, close to 146C. Fully developed leaves, lower surface: Close to 147B; venation, close to 147D.

*Petiole.*—Length: About 3.3 cm. Diameter: About 3 mm. Texture, upper and lower surfaces: Pubescent. Color, upper and lower surfaces: Close to 146A to 146B.

Flower description:

*Flower type and arrangement.*—Semi-double rotate flowers arranged in axillary racemes; flowers face mostly outwardly.

*Fragrance.*—None detected.

*Quantity of flowers.*—Freely flowering habit; about 26 flowers per inflorescence.

*Flowering season.*—Plants flower continuously from late summer into the autumn in The Netherlands.

*Flower longevity.*—Flowers last about five days on the plant; flowers not persistent.

*Inflorescence height.*—About 31 cm.

*Inflorescence diameter.*—About 9.1 cm.

*Flower diameter.*—About 6 cm.

*Flower depth (height).*—About 3.1 cm.

*Flower buds.*—Length: About 1.1 cm. Diameter: About 1.4 cm. Shape: Oblate. Color: Close to 148C to 148D; towards the base, close to 147B.

*Petals.*—Quantity per flower: Five in a single whorl. Length: About 2.7 cm. Width: About 2.8 cm. Shape: Broadly obovate to flabellate. Apex: Rounded. Base: Attenuate. Margin: Entire. Texture, upper and lower surfaces: Smooth, glabrous. Color: When opening, upper and lower surfaces: Close to 70B. Fully opened, upper surface: Close to 64A to 64B; towards the base, close to 70C; color becoming closer to 61A and 64A with development. Fully opened, lower surface: Close to 64B and 70B; towards the base, close to 70C.

*Petaloids.*—Quantity per flower: About 60 in numerous whorls. Length: About 1.8 cm. Width: About 1 cm. Shape: Narrowly obovate. Apex: Rounded, emarginate. Base: Attenuate. Margin: Entire. Texture, upper and lower surfaces: Smooth, glabrous. Color: When opening, upper and lower surfaces: Close to 70B. Fully opened, upper and lower surfaces: Close to 64A to 64B; towards the base, close to 70C.

*Sepals.*—Quantity per flower: About 14 in two whorls. Length: About 1 cm to 1.2 cm. Width: About 4 mm to 9 mm. Shape: Ovate to narrowly ovate. Apex: Broadly acute to acute. Base: Broadly cuneate. Margin: Entire. Texture, upper and lower surfaces: Densely pubescent. Color: When opening, upper and lower surfaces: Close to 147B. Fully opened, upper and lower surfaces: Close to 147B.

*Peduncles.*—Length: About 30.4 cm. Diameter: About 2.5 mm. Strength: Strong. Angle: Mostly erect. Texture: Smooth. Color, upper and lower surfaces: Close to 144A to 144B.

*Pedicels.*—Length: About 1 cm. Diameter: About 1.5 mm. Strength: Moderately strong. Angle: About 45° from the peduncle axis. Texture: Smooth. Color, upper and lower surfaces: Close to 144A to 144B.

*Reproductive organs.*—Androecium: Stamen quantity per flower: About 40. Filament length: About 8 mm. Filament color: Close to 160D. Anther length: About 1 mm. Anther shape: Irregularly reniform. Anther color: Close to N186B to N186C. Pollen amount: Scarce. Pollen color: Close to 11D. Gynoecium: Pistil quantity per flower: About ten. Pistil length: About 1.3 cm. Stigma shape: Club-shaped, narrow. Stigma color: Close to 71A to 71B. Style length: About 9 mm. Style color: Close to 150C to 150D. Ovary color: Close to 150B to 150C.

*Fruit and seed.*—Fruit and seed development have not been observed on plants of the new *Malva*.

Disease/pest resistance: Plants of the new *Malva* have not been observed to be resistant to pathogens and pests common to *Malva* plants.

Garden performance: Plants of the new *Malva* have exhibited good tolerance to rain and wind, have been observed to be hardy to USDA Zone 7 and to tolerate high temperatures of about 35° C.

It is claimed:

1. A new and distinct *Malva* plant named 'Poetry' as illustrated and described.

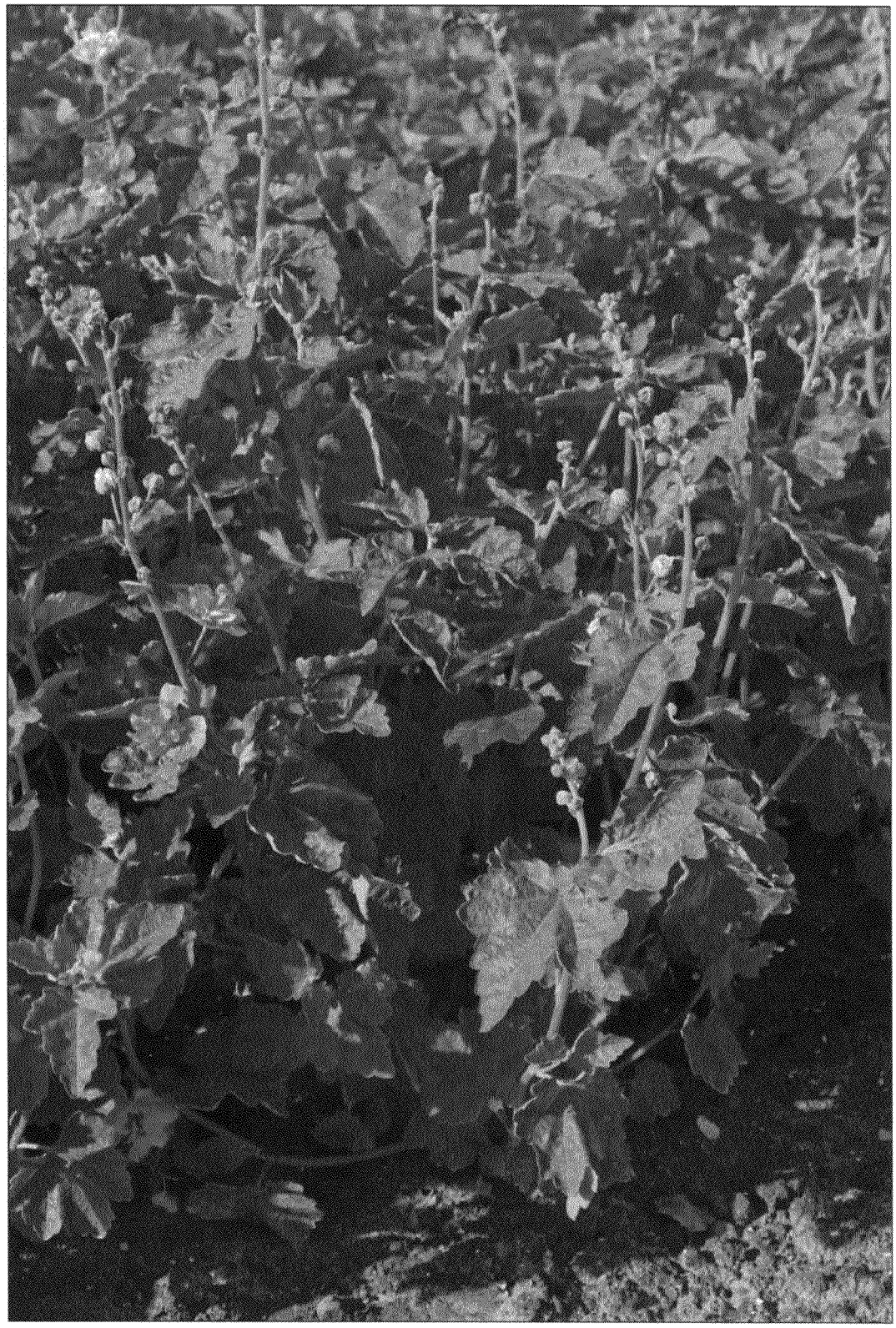

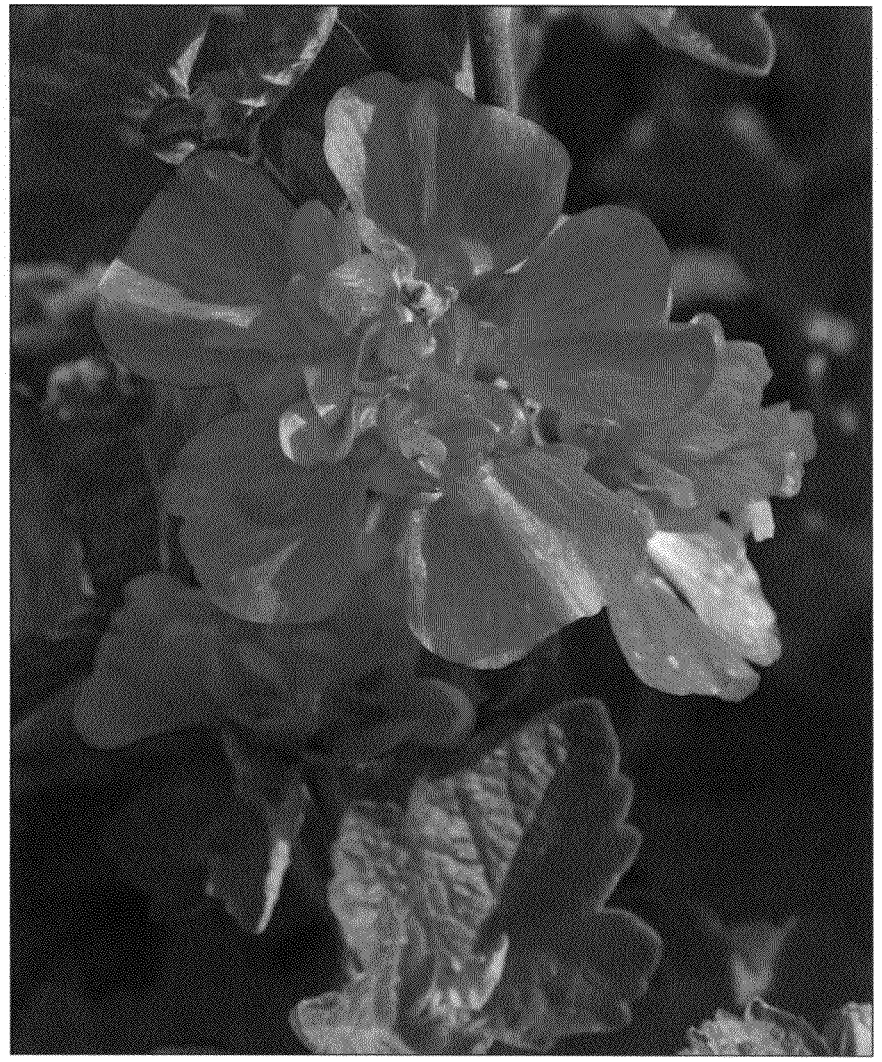
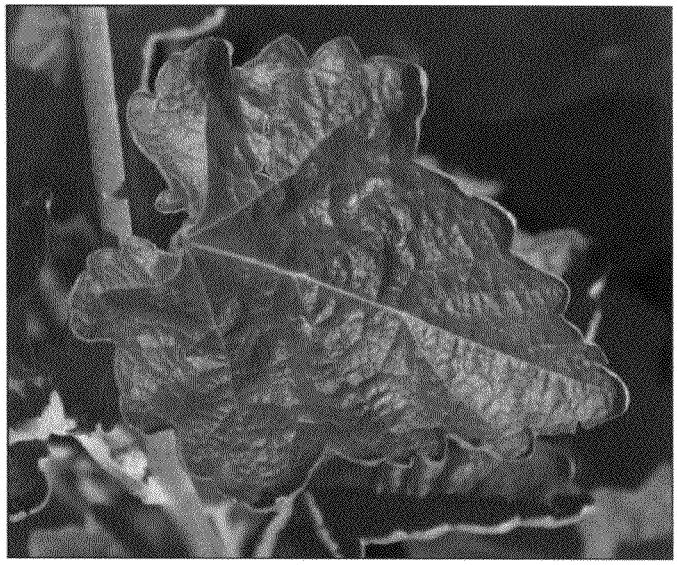

* * * * *